United States Patent
Syed et al.

(10) Patent No.: US 9,335,251 B2
(45) Date of Patent: May 10, 2016

(54) FOULING LAYER DETECTION ON AN ENVIRONMENTAL SENSOR

(71) Applicant: NXP B.V., Eindhoven (NL)

(72) Inventors: Aly Aamer Syed, Deurne (NL); Manvi Agarwal, Eindhoven (NL)

(73) Assignee: NXP B.V., Eindhoven (NL)

( * ) Notice: Subject to any disclaimer, the term of this patent is extended or adjusted under 35 U.S.C. 154(b) by 212 days.

(21) Appl. No.: 14/064,607

(22) Filed: Oct. 28, 2013

(65) Prior Publication Data

US 2014/0151538 A1 Jun. 5, 2014

(30) Foreign Application Priority Data

Nov. 30, 2012 (EP) ..................................... 12194982

(51) Int. Cl.
*G01N 21/17* (2006.01)
*G01N 21/15* (2006.01)
*G01N 21/94* (2006.01)
*G01N 21/53* (2006.01)

(52) U.S. Cl.
CPC ................ *G01N 21/17* (2013.01); *G01N 21/15* (2013.01); *G01N 21/94* (2013.01); *G01N 21/53* (2013.01); *G01N 2021/157* (2013.01); *G01N 2021/945* (2013.01)

(58) Field of Classification Search
CPC .................. G01N 2021/157; G01N 2021/945; G01N 21/15; G01N 21/17; G01N 21/53; G01N 21/94
See application file for complete search history.

(56) References Cited

U.S. PATENT DOCUMENTS

| 5,998,782 | A | 12/1999 | Koyama et al. |
| 6,118,383 | A * | 9/2000 | Hegyi .......................... 340/602 |
| 6,376,824 | B1 * | 4/2002 | Michenfelder et al. .... 250/214 R |
| 7,652,586 | B2 | 1/2010 | Baller et al. |
| 8,144,330 | B2 | 3/2012 | Itoh |

FOREIGN PATENT DOCUMENTS

| CN | 202451025 U | 9/2012 |
| DE | 102 14 421 A1 | 10/2003 |
| DE | 103 08 544 A1 | 10/2003 |
| DE | 10 2006 039 034 A1 | 2/2008 |
| EP | 1457763 A2 | 9/2004 |
| JP | 2002296342 A | 10/2002 |

OTHER PUBLICATIONS

Extended European Search Report for EP Patent Appln. No. 12194982.0 (May 8, 2013).

* cited by examiner

*Primary Examiner* — Francis M Legasse, Jr.

(57) ABSTRACT

An environmental sensor is disclosed. The environmental sensor includes a semiconductor substrate including a light sensor, a surface through which ambient light can pass to reach a light sensor and a light source operable to illuminate the surface, whereby at least some of the light from the light source is reflected by the surface onto the light sensor. The environmental sensor is operable to determine the presence of a fouling layer on the surface by comparing measurements of ambient light and reflected light by the at least one light sensor.

20 Claims, 4 Drawing Sheets

FOULING LAYER DETECTION ON AN ENVIRONMENTAL SENSOR

CROSS-REFERENCE TO RELATED APPLICATIONS

This application claims the priority under 35 U.S.C. §119 of European patent application no. 12194982.0, filed on Nov. 30, 2012, the contents of which are incorporated by reference herein.

BACKGROUND OF THE INVENTION

This invention relates an environmental sensor. This invention also relates to a method of operating an environmental sensor.

Environmental sensors can be used for the determination of various physical parameters such as temperature, light intensity, pressure, strain, shock, moisture, carbon dioxide and many other gases in various environments such as buildings (e.g. houses, offices, warehouses, green houses etc.), vehicles such as cars and trucks (for example in the passenger compartment, or in the engine of the vehicle), in-vitro and even in-vivo applications.

There is a clear society trend to make homes and building smart, meaning that the ecological footprint of homes and buildings must be reduced as much possible. A lot of energy in buildings and homes is used in heating, ventilation and air conditioning (HVAC). A carbon dioxide sensor can, for example, monitor the quality of the air and together with a temperature and humidity sensor feedback the results to the HVAC system that then can take appropriate actions. Additional energy reduction can be achieved by environmental sensors that measure the light intensity in a room and adjust the artificial lighting accordingly. All these environmental sensors can also be connected through networks. In this way lighting, temperature, fresh air and humidity can be dynamically adjusted rather than following a pre-programmed regime and in this way the ecological footprint can be reduced.

It is also very well thinkable that environmental sensors such as pressure, airborne particles, carbon dioxide, and carbon monoxide sensors, and sensors to monitor breath composition will increasingly appear in mobile devices such as mobile telephones or tablets.

Another application domain is in the car, where the drivers and passengers want to monitor the quality of air for contaminants and particles and where the control systems then can take appropriate action such as shutting down or filtering in coming air.

Another application domain is in the white good market segment. For example, moisture and grease layers in refrigerators can indicate the level of hygiene in the refrigerator. An environmental sensor in the refrigerator, that can monitor levels of for example NH3 or other freshness of food related gases, can malfunction in case moisture or grease layers accumulate.

In many of these applications the sensors will be used for years, aiming for undisturbed functioning as an autonomous device. During that time and while exposed to the ambient it is very well possible that the surface of the sensor will see a deposit of materials such as dust, oil, salt, grease etc. For optical (light intensity measurements) as well as chemical sensors (moisture, gases, liquids) and mechanical sensors (e.g. MEMS based devices) such as pressure sensors including a diaphragm, these fouling layers can severely impact proper reading of the parameter.

Although there have been reports on the detection of fouling layers (U.S. Pat. No. 5,998,782; EP 1457763; DE 102006039034, JP 2002296342, U.S. Pat. No. 8,144,330 and U.S. Pat. No. 7,652,586) none of those are in the field of environmental sensors.

SUMMARY OF THE INVENTION

Particular and preferred aspects of the invention are set out in the accompanying independent and dependent claims. Combinations of features from the dependent claims may be combined with features of the independent claims as appropriate and not merely as explicitly set out in the claims.

According to an aspect of the invention there is provided an environmental sensor comprising a semiconductor substrate including a light sensor; a surface through which ambient light can pass to reach a light sensor, a light source operable to illuminate the surface, whereby at least some of the light from the light source is reflected by the surface onto the light sensor. The environmental sensor is operable to determine the presence of a fouling layer on the surface by comparing measurements of ambient light and reflected light by the at least one light sensor.

According to another aspect of the invention, there is provided a method of operating an environmental sensor comprising a semiconductor substrate, a light sensor, a surface through which ambient light can pass and a light source operable to illuminate the surface, whereby at least some of the light from the light source is reflected by the surface onto the light sensor. The method includes determining the presence of a fouling layer on the surface by comparing measurements of ambient light and reflected light by the at least one ambient light sensor.

Environmental sensors will inherently be exposed to the environment and therefore can suffer fouling layer accumulation. These fouling layers can inhibit correct reading of the parameters of interest. According to embodiments of the invention, it is not only possible to implement fouling layer detection in environmental sensors comprising semiconductor substrates, but it is also possible to take advantage of semiconductor substrate features such as miniaturization, low cost manufacturing and multiple sensor integration.

An environmental sensor according to an embodiment of the invention can combine fouling layer detection with sensors such as a standalone smoke or a standalone CO or $CO_2$ sensor.

Whereas in some examples the environmental sensor can comprise a standalone light source and a standalone light detector, it is also possible to combine the light source and the light detector in a common semiconductor substrate, for a more compact construction and to allow lower cost manufacturing.

The semiconductor substrate in an environmental sensor can enable many more sensors to be integrated. In addition to a light sensor it is, according to an embodiment of the invention, possible to further integrate pressure, temperature and gas sensors in one common semiconductor substrate.

In one example, the light source can be constructed as a light emitting diode (LED). This allows a more compact and power efficient construction.

The light sensor can analyse a frequency spectrum of the received light to differentiate between different kinds of ambient light sources. This differentiation can be utile when the environmental sensor is used in a system that regulates the lighting conditions in a building or a room.

The environmental sensor can be packaged (e.g. by locating the semiconductor substrate and any other components of the sensor in a semiconductor package that allows access of the sensor to the surrounding environment). In such embodiments, the surface can comprise a window in the package material.

Another way to provide a surface for the environmental sensor is to deposit on the semiconductor substrate a material (for example, an oxide) that can serve as the surface. In this way the packaging of the sensor can be simplified (since no separate provision (such as a window) need be made in the package itself to form the reflecting surface).

The surface comprising a layer of material deposited on the semiconductor substrate comprises silicon nitride, silicon oxynitride or silicon dioxide. These are materials that are in common use in semiconductor manufacturing further enabling low cost manufacturing.

The environmental sensor can form part of an environmental management system, either as a stand-alone sensor, or as part of a network of sensors in a building automation system.

According to an embodiment of the invention, there is a method to determine the intensity of the reflected light in the presence of ambient light is to do a first intensity measurement with the light source off and do a second measurement with the light source on. By subtracting the two intensities the reflected light intensity will remain.

According to an embodiment of the invention, there is provided a method to measure the intensity of the reflected light by the surface on which there is no fouling present and in the absence of ambient light, for use as a calibrated light intensity characteristic for a clean transparent surface. This intensity can be used as a reference value to compare with intensity values of the reflected light whereas there is a fouling layer present.

According to an embodiment of the invention, frequency analysis of the ambient and reflected light can be used to differentiate between different kinds of ambient light sources. This differentiation can be utilized when the environmental sensor is used to in a system that regulates the lighting conditions in a building or a room.

According to an embodiment of the invention, frequency analysis of the ambient and reflected light can be used to determine factors such as the structure, composition or thickness of a fouling layer.

BRIEF DESCRIPTION OF THE DRAWINGS

Embodiments of the present invention will be described hereinafter, by way of example only, with reference to the accompanying drawings in which like reference signs relate to like elements and in which.

DETAILED DESCRIPTION

Embodiments of the present invention are described in the following with reference to the accompanying drawings.

Figure 1:
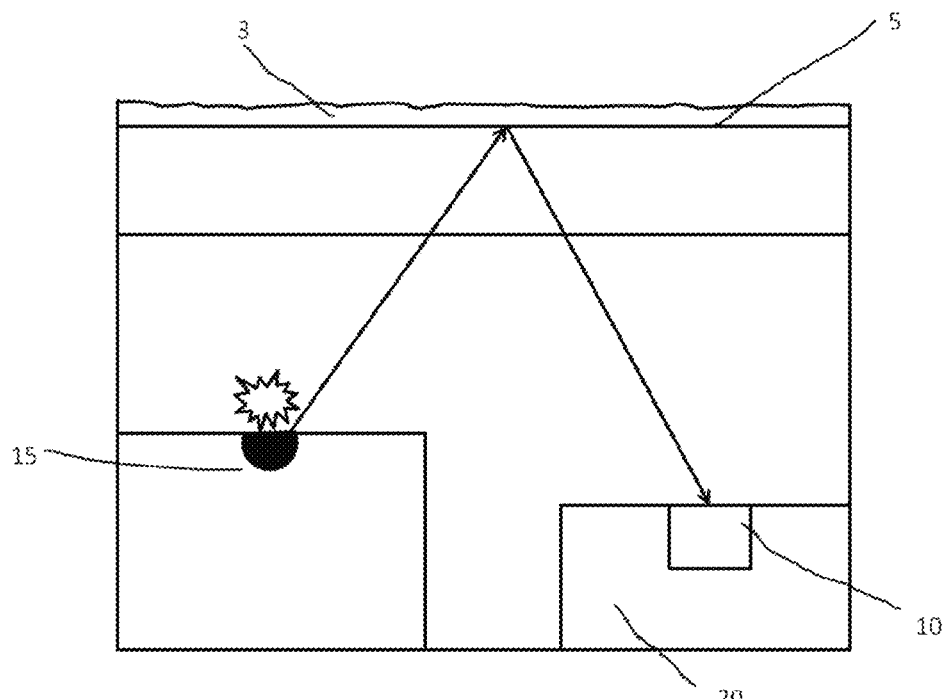
FIG. 1 shows a first embodiment of the invention with light source and light sensor on different substrates.

FIG. 1 schematically illustrates a first embodiment of the invention. In accordance with this embodiment, there is provided a light source 15, a light sensor 10 in a semiconductor substrate 20 and a surface 5. The surface 5 comprises a piece of material (for example quartz) through which light can pass. It can have a rectangular or circular or other shape. The surface 5 is exposed to the environment and can therefore accumulate a fouling layer 3. The fouling layer 3 material can be various substances such as grease, dust, particles, oil and salt coming from various sources such as the wind, industrial activities and smoking.

Ambient light from the surrounding environment can pass through the fouling layer 3 and the surface 5 and can reach the light sensor 10. A portion of the light originating from the light source 15 can be reflected by the fouling layer 3 to reach the light sensor 10. In the semiconductor substrate 20, peripheral circuitry for measurement programming and signal processing can be integrated. This allows that a first measurement of intensity at t=t1 is performed in which ambient light passes through the fouling layer and through the surface 5, while the light source 15 is turned off and results in a measured intensity I1. Then a second measurement of intensity at t=t2 can be performed while the light source 15 is turned on and results in a measured intensity I2. Subsequently I1 can be subtracted from I2 in the signal processing part of the circuitry and the result, Ic=I2−I1, is then a measure of the intensity of the reflected light. The intensity of light reflected by the surface 5 depends on the material of the surface 5 itself but also on the presence of a fouling layer. It is expected that the amount of light that is received by the light sensor when a fouling layer is present will change compared to the situation when no fouling layer is present because part of the light can now also be scattered, reflected or absorbed by the fouling layer. Therefore a change in received light by the light sensor can be a measure for the presence of a fouling layer.

There should not be a too large time difference between t1 and t2, as a reliable determination of Ic is only possible if the intensity of the ambient light has not changed substantially between t1 and t2. A typical time difference between t1 and t2 should be certainly less than a second but can be as small as a few nanoseconds. For example when the environmental sensor is in a room where there is only artificial lighting then the intensity of the ambient light will not fluctuate a lot. However, when the environmental sensor is placed outdoors, strong light fluctuations can occur, for example when a cloud is blocking sun light. In a further refinement, it is also possible to record the intensity of the reflected light, Ir, on a new, unused environmental sensor that has not been exposed to the environment and thus no fouling layer will be present. The difference Ic−Ir is then also a measure for the amount of fouling layer 3 accumulated on the surface 5.

The light source 15 in this embodiment can be made in several ways but a light emitting diode (LED) can provide a very energy efficient solution. Alternatively it is also possible to construct the light source 15 using OLED technology.

It is also possible to use a plurality of light sources that generate light at different wavelengths. For example AlGaAs generates predominantly infra red light whereas InGaN can generate predominantly ultra violet light. Performing measurements at more than one wavelength can be advantageous in cases where more details about the fouling layer are desirable.

According to the first embodiment, the light sensor is integrated in a semiconductor substrate. The light sensor can be a simple device such as a light dependent resistor (LDR) or a more advanced device such as one based on photodiodes or phototransistors in the semiconductor substrate that control the flow of holes or electrons across their PN junctions. By combining refraction grids on top of the semiconductor substrate it is possible to let only light at a specific wavelength pass on to the light sensor. The grids can be made during the manufacturing of the different devices in semiconductor substrate from parallel lines made out of polysilicon, dielectric or metal materials. By proper choice of the line spacings, light with different wavelengths can be tuned to reach the light sensor. By combining several light sensors with different grids it is possible to generate an intensity profile at different wavelengths of the received light. This feature can be particularly useful in situations where the nature of the fouling layer is known, for example it is known that the fouling layer can be either of an organic nature such as grease or oil or that the fouling layer can be condensation of water. In this case a wavelength will be chosen such that the light is absorbed by either the organic layer or the water layer. Further refinement of this characterization is anticipated when models and algorithms are included in the on-board peripheral circuitry of the environmental sensor. In the models and algorithms, information can be stored at which wavelengths of the ambient light that passes through the fouling layer, absorption will occur.

Figure 2:
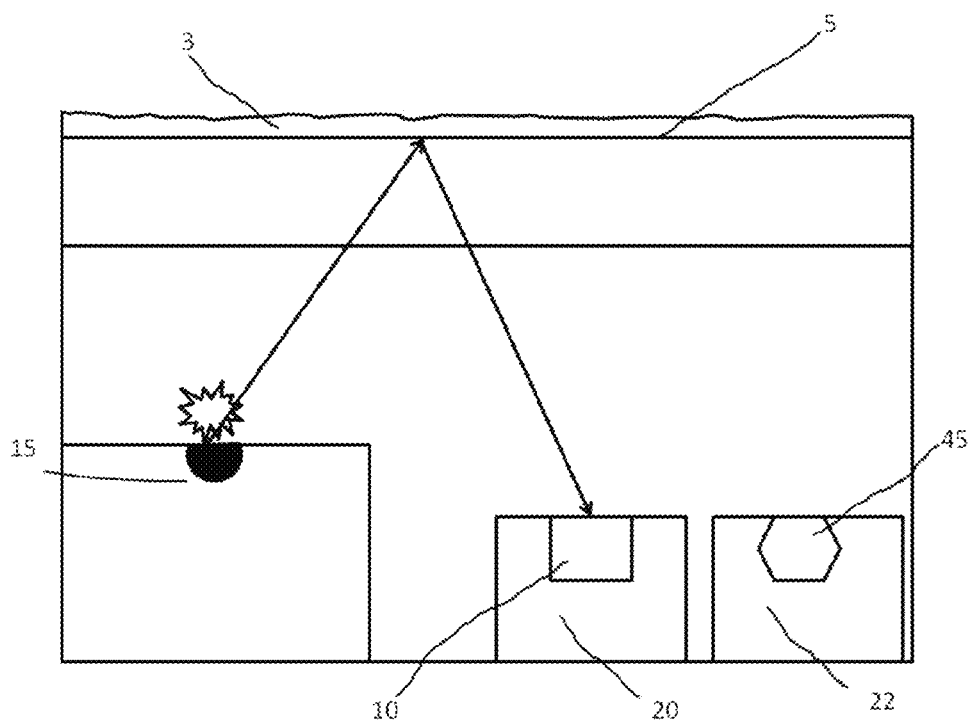
FIG. 2 shows a second embodiment of the invention in which in addition to embodiment 1 a temperature sensor on a different semiconductor substrate is added.

FIG. 2 schematically illustrates a second embodiment of the invention. In accordance with this embodiment, there is provided a light source 15, a light sensor 10 in a semiconductor substrate 20, a surface 5 and a further sensor 45 (for example a temperature sensor) also in a substrate 22. In this way it is possible to extend the environmental sensor with many more sensors that by nature are difficult to integrate in one common semiconductor substrate. For example the light source can be made in a GaN substrate, the light sensor could be made in a CdS substrate and the temperature sensor in a silicon substrate.

Figure 3:
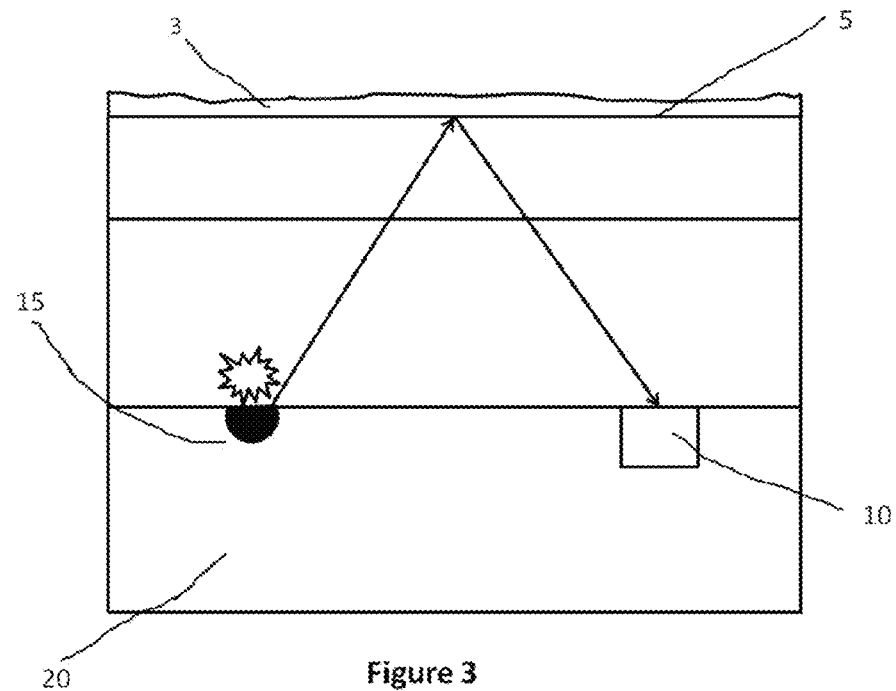
FIG. 3 shows a third embodiment of the invention whereas light sensor and light source are integrated in a common substrate.

FIG. 3 schematically illustrates a third embodiment of the invention. In accordance with this embodiment, there is provided a light source 15, a light sensor 10 in a semiconductor substrate 20 and a surface 5. According to this embodiment of the invention, the light source 15 and the light sensor are integrated in a common semiconductor substrate. This embodiment takes advantage of semiconductor mass volume manufacturing leading to very low costs. Another advantage is that the environmental sensor can be more compact than in the first embodiment. In this embodiment it is also possible to have the integrated light source 15 in the form of a light emitting diode (LED).

Figure 4:
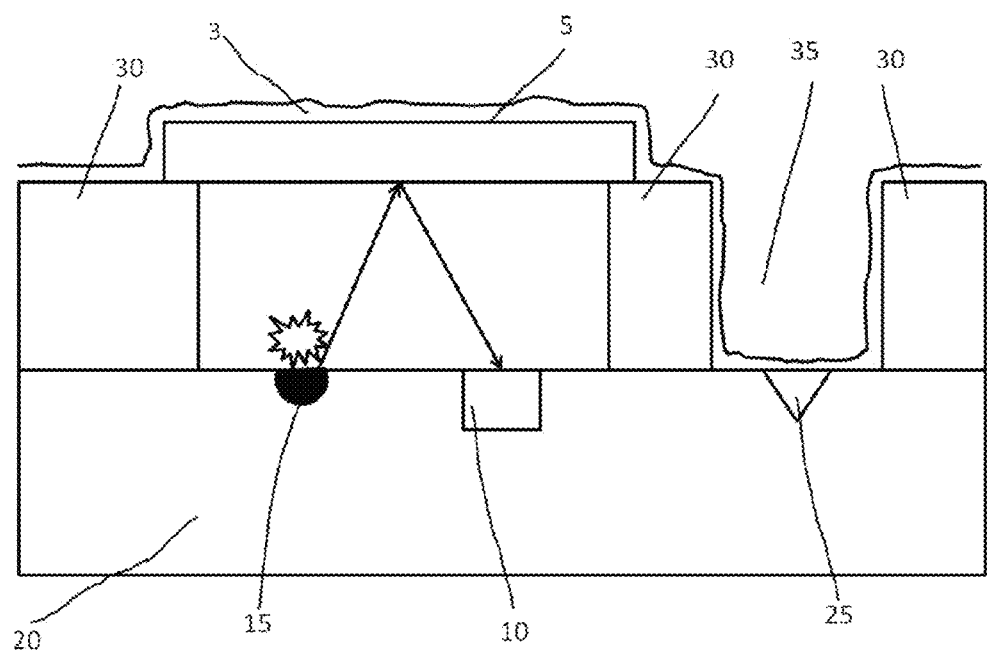
FIG. 4 shows a fourth embodiment of the invention with an integrated moisture sensor.
Figure 5:
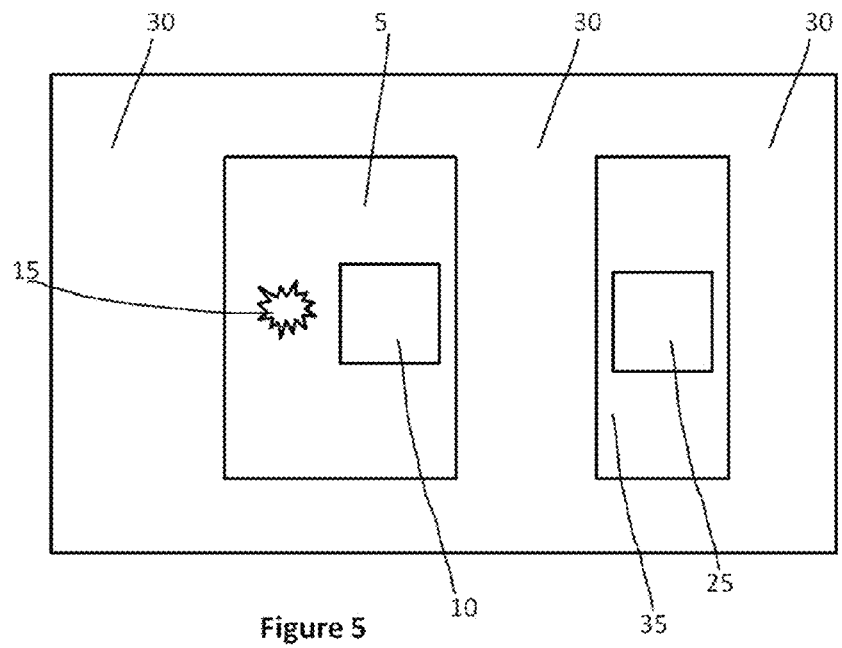
FIG. 5 shows a top view of the environmental sensor of FIG. 4.

FIG. 4 schematically illustrates a fourth embodiment of the invention. FIG. 5 provides a top view of embodiment 4. In accordance with this embodiment, there is provided a light source 15, a light sensor 10 in a semiconductor substrate 20, a surface 5, a moisture sensor 25 and a package 30 with opening 35 to expose the moisture sensor to the ambient. Also there is a foiling layer 3 that covers the entire region exposed to the environment. The moisture sensor can be realized by a measurement of the capacitance of a capacitor in which the two electrodes are formed with two interdigitated fingers and where the dielectric material can be a moisture sensitive polymer. When moisture is taken up by the polymer there will be a change in its dielectric constant and that will cause a change in the measured capacity.

The light source 15, the light sensor 10 and the moisture sensor 25 in this example are all integrated in one common semiconductor substrate, therefore taking the same advantage as in embodiment 3 in terms of compactness as well as low cost manufacturing. According to this embodiment of the invention, the environmental sensor is provided within a package 30, as is quite common in semiconductor devices, in order to protect the environmental sensor against mechanical, chemical and other influences. The package supports a surface 5 to allow for the same measurements as described in embodiment 1 and 2. As mentioned earlier the surface 5 can be made of materials such as quartz and must allow the passing of ambient light. The size of the surface 5 can be larger than the opening in the package so that it can be sealed on top of the package with the aid of a compatible glue. The package provides further an opening 35 to enable contact of the integrated moisture sensor to the environment.

Figure 6:
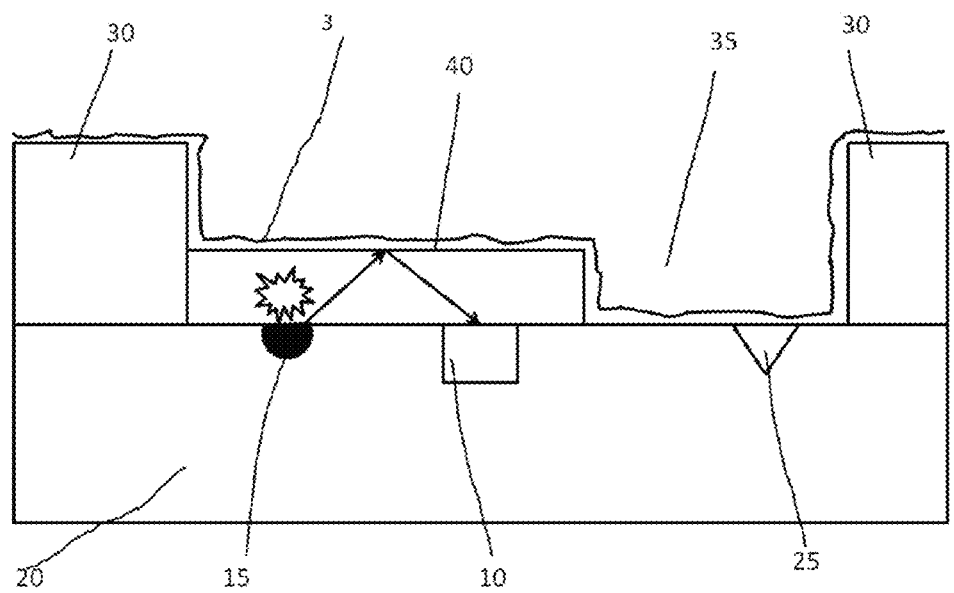
FIG. 6 shows a fifth embodiment of the invention with the surface deposited on the semiconductor substrate.
Figure 7:
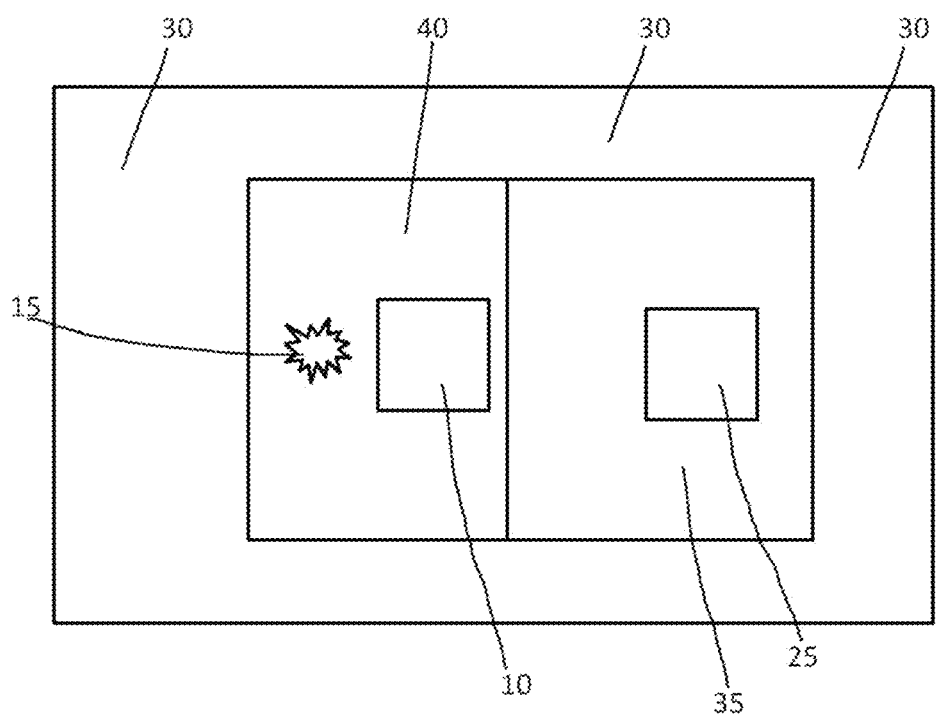
FIG. 7 shows a top view of the environmental sensor of FIG. 6.

FIG. 6 schematically illustrates a fifth embodiment of the invention. In FIG. 7 a top view of the fifth embodiment is given. In accordance with this embodiment, there is provided a light source 15, a light sensor 10 in a semiconductor substrate 20, a surface 40, a package 30 and a moisture sensor 25. The package also provides an opening 35 to provide ambient contact for the moisture sensor and for the surface 5. The difference with the third embodiment is the way the surface is provided. According to this embodiment of the invention the surface is deposited directly on the semiconductor substrate and can be made of materials that are standard in semiconductor processing, for example a layer of silicon-oxynitride (SiON) or silicon dioxide (SiO2). The layer can be deposited using chemical vapour deposition or plasma enhanced chemical vapour deposition techniques or spin-on-glass techniques. The thickness of the SiON or SiO2 layers is not critical, but typical values will be in the range of 0.5 to 1.0 microns. If needed, standard patterning (lithography and etching) techniques can be used to free up the substrate where needed for the moisture sensor. This embodiment simplifies the packaging of the environmental sensor.

It is known that many styles of environmental sensors can be made in CMOS technology. For example shock, pressure, temperature, light, moisture and gases have been reported. In embodiments 1 and 2 sensors that do not need a direct opening to the environment like the shock, temperature and light sensors can be directly integrated in the semiconductor substrate. In embodiments 3 and 4 it is possible to add to the shock, temperature and light sensor also sensors like the pressure, moisture and the gas sensors because these will require a direct opening 35 to the ambient. Because these sensors can be impacted by fouling layers, having an environmental sensor equipped with fouling layer detection is very advantageous.

The fouling detection integrated with some of the sensors mentioned above can be very utile in environmental management systems for homes and buildings. The environmental management system (EMS) will contain environmental sensors that can monitor parameters like the temperature, the humidity, the light levels and the CO2 concentration in the air. The environmental sensors can be part of a network of sensors placed throughout the building. In such an application it is desirable to integrate other circuitry in the semiconductor substrate that can communicate, wireless or wired, with the environmental management system and transmit output signals. In these management systems the output signals of the environmental sensors can be used to adjust heating or cooling, humidifiers, fresh air inlets, artificial lighting intensity on and so forth on a continuous and demand basis. It is clear that the environmental sensors in the homes and buildings will be in use for many years. During that period the sensor can track the accumulation of fouling layers. This can be done if a non-volatile memory has been integrated in the semiconductor substrate. This memory can then be used to log the data that is provided by the measurements over time. The accumulation can be reported back to the management system that can then take appropriate actions for example initiate maintenance or, in case of unexpected fast accumulation or accumulation of an unexpected composition, explore possible culprits.

Other fields of application are in mobile phones or tablets, white goods, in automotive but also in in-vivo and in-vitro situations.

For example, in a refrigerator there can be heavy build up of water condensation and grease layers. This can cause malfunctioning of the apparatus with possibly health hazards. The application of an environmental sensor can detect the accumulation of such layers and give a signal that cleaning is needed.

In an automobile similar principles as described above in the case of home and building environmental management system may also apply. For example, if in front of the car there is another vehicle that produces heavy smoke from its exhaust, then an environmental detector can detect the particles in the air or perhaps elevated levels of CO and close subsequently the fresh air intake channels of the car.

In mobile phones or tablets it can be possible to include environmental sensors to measure for example pressure or the CO2 levels in a room.

In all the embodiments and example given above it is assumed that there is an accumulation of fouling layers. However, it is very well thinkable that there are applications where the environmental sensor is actual in a situation where etching of the surface can occur. For example, in case the environmental sensor is used to monitor certain aspects of industrial waste water, the surface can be etched by an acid and the surface texture can change. This will also induce a change in the reflected light intensity and this signal can then be used for monitoring purposes as well or to give a warning signal that the integrity of the environmental sensor is at stake. In such examples, the fouling layer comprises the part of the surface that is affected (e.g. etched).

Accordingly, there has been described an environmental sensor and a method of operating an environmental sensor. The environmental sensor includes: a semiconductor substrate including a light sensor; a surface through which ambient light can pass to reach a light sensor, a light source operable to illuminate the surface, whereby at least some of the light from the light source is reflected by the surface onto the light sensor. The environmental sensor is operable to determine the presence of a fouling layer on the surface by comparing measurements of ambient light and reflected light by the at least one light sensor.

Although particular embodiments of the invention have been described, it will be appreciated that many modifications/additions and/or substitutions may be made within the scope of the claimed invention.

The invention claimed is:

1. An environmental sensor comprising:
a semiconductor substrate including a light sensor;
a surface through which ambient light can pass to reach the light sensor, and
a light source configured to illuminate the surface, whereby at least some light from the light source is reflected by the surface onto the light sensor, wherein the environmental sensor is configured to determine a presence of a fouling layer on the surface by comparing measurements of the ambient light and the reflected light by the light sensor to the reflected light of an unused environmental sensor that has not been exposed to an environment.

2. The environmental sensor of claim 1, comprising:
a second sensor.

3. The environmental sensor of claim 1, wherein the light sensor and the light source are integrated in a common semiconductor substrate.

4. The environmental sensor of claim 2, wherein the light sensor, the light source and the second sensor are each integrated on a common substrate, the second sensor is located in a first region of the substrate and the light source and light sensor are located in a second region of the substrate, the second region is shielded from the environment by the surface, and the first region is exposed to an environment.

5. The environmental sensor of claim 1, wherein the light source is an LED device.

6. The environmental sensor of claim 1, configured to analyze a frequency spectrum of the reflected light to differentiate between different kinds of ambient light sources.

7. The environmental sensor of claim 1, wherein the surface comprises:
a window in a package of the environmental sensor.

8. The environmental sensor of claim 1, wherein the surface comprises:
a material deposited on the semiconductor substrate.

9. The environmental sensor of claim 8, wherein the material deposited on the semiconductor substrate comprises silicon nitride, silicon oxynitride, or silicon dioxide.

10. An environmental management system comprising at least one environmental sensor according to claim 1.

11. A method of operating an environmental sensor comprising a semiconductor substrate including a light sensor, a surface through which ambient light can pass to reach the light sensor, and a light source configured to illuminate the surface, whereby at least some light from the light source is reflected by the surface onto the light sensor, the method comprising:
determining the presence of a fouling layer on the surface by comparing measurements of the ambient light and the reflected light by the light sensor to the reflected light of an unused environmental sensor that has not been exposed to an environment.

12. The method of claim 11 further comprising:
making a first measurement intensity of the ambient light that passes the surface the light source is turned off;
making a second measurement intensity of the light reaching the light sensor the light source is turned on;
subtracting the first measured intensity from the second measured intensity; and
using the result of the subtraction to determine the intensity of the reflected light.

13. The method of claim 11, comprising:
measuring intensity, by the light sensor, of light from the light source reflected by the surface, on which no fouling layer is present, without the ambient light, for use as a calibrated light intensity characteristic for a clean transparent surface.

14. The method of claim 11, comprising:
analyzing a frequency spectrum of the reflected light to differentiate between different kinds of ambient light sources.

15. The method of claim 11, comprising:
using frequency characteristics of the ambient light and the reflected light to determine a structure or thickness of the fouling layer.

16. The environmental sensor of claim 2, wherein the second sensor is a temperature sensor.

17. The environmental sensor of claim 2, wherein the second sensor is a moisture sensor.

18. The environmental sensor of claim 1, wherein the environmental sensor is configured to determine whether the fouling layer is an organic layer or a water layer.

19. The environmental sensor of claim 1, wherein the environmental sensor is configured to record wavelengths that result in absorption of the ambient light by the fouling layer.

20. The environmental sensor of claim 1, wherein the environmental sensor is configured to measure a rate of accumulation of the fouling layer.

* * * * *